US012716884B2

(12) United States Patent
Hoshino et al.

(10) Patent No.: US 12,716,884 B2
(45) Date of Patent: Aug. 25, 2026

(54) QUALITY EVALUATION METHOD, MANUFACTURING SYSTEM OF SILICON FOR EVALUATION, MANUFACTURING METHOD OF SILICON FOR EVALUATION, AND SILICON FOR EVALUATION

(71) Applicant: Shin-Etsu Chemical Co., Ltd., Tokyo (JP)

(72) Inventors: Naruhiro Hoshino, Niigata (JP); Shigetoshi Yamagishi, Niigata (JP); Atsushi Yoshida, Niigata (JP); Masahiko Ishida, Niigata (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 778 days.

(21) Appl. No.: 18/146,304

(22) Filed: Dec. 23, 2022

(65) Prior Publication Data

US 2023/0236165 A1 Jul. 27, 2023

(30) Foreign Application Priority Data

Jan. 25, 2022 (JP) ................................ 2022-009548

(51) Int. Cl.

*C23C 16/24* (2006.01)
*C01B 33/03* (2006.01)
*C30B 25/02* (2006.01)
*C30B 29/06* (2006.01)
*G01N 33/00* (2006.01)

(52) U.S. Cl.

CPC ............ *G01N 33/39* (2024.05); *C01B 33/03* (2013.01); *C23C 16/24* (2013.01); *C30B 25/02* (2013.01); *C30B 29/06* (2013.01)

(58) Field of Classification Search

CPC ........ G01N 33/39; C01B 33/03; C23C 16/24; C30B 25/02

See application file for complete search history.

(56) References Cited

U.S. PATENT DOCUMENTS 5,483,918 A * 1/1996 Kobayashi .............. C30B 25/02 117/92

FOREIGN PATENT DOCUMENTS

| | | | |
|---|---|---|---|
| EP | 0445036 | A1 | 9/1991 |
| EP | 2636767 | A1 | 9/2013 |
| JP | H03252397 | A | 11/1991 |
| JP | H05-58789 | A | 9/1993 |
| JP | 2014-114184 | A | 6/2014 |
| JP | 2016145118 | A | 8/2016 |

OTHER PUBLICATIONS

Office Action in Japanese patent application No. 2022-009548, issued on Apr. 1, 2025.

* cited by examiner

*Primary Examiner* — Nathan T Leong
(74) *Attorney, Agent, or Firm* — Ladas & Parry, LLP

(57) ABSTRACT

A quality evaluation method has a step of producing a silicon for evaluation in which a single crystal silicon is grown to extend radially from a core wire 9 while polycrystalline silicon is grown in a reactor 20; and a step of performing an evaluation using the single crystal silicon.

4 Claims, 2 Drawing Sheets

QUALITY EVALUATION METHOD, MANUFACTURING SYSTEM OF SILICON FOR EVALUATION, MANUFACTURING METHOD OF SILICON FOR EVALUATION, AND SILICON FOR EVALUATION

TECHNICAL FIELD

The present invention relates to a quality evaluation method, a manufacturing system of silicon for evaluation, and a manufacturing method of silicon for evaluation that use an aspect in which polycrystalline silicon is grown on a core wire in a reactor, and the present invention relates to silicon for evaluation.

The present application claims the priority of Japanese Patent Application No. 2022-009548 filed on Jan. 25, 2022, the contents of which are entirely incorporated by reference.

BACKGROUND ART

Polycrystalline silicon is a raw material of single crystal silicon for semiconductors or silicon for solar cells. As a production method of polycrystalline silicon, the Siemens method is known. The Siemens method is a method in which, generally by bringing a silane source gas into contact with a heated silicon core wire, polycrystalline silicon is deposited on the surface of the silicon core wire by using a chemical vapor deposition (CVD) method.

In the Siemens method, two silicon core wires and one silicon core wire are respectively assembled in a vertical direction and a horizontal direction in a shape of a shrine gate, and the both ends of the shrine gate-shaped silicon core wire are each connected to a core wire holder and are fixed to a pair of metal electrodes disposed on a bottom plate. In general, a plurality of sets of the shrine gate-shaped silicon core wires are arranged in a reaction furnace.

The shrine gate-shaped silicon core wire is energized and thereby heated to a deposition temperature, and, for example, a gas mixture of trichlorosilane and hydrogen as a raw material gas is brought into contact with the silicon core wire, so that silicon is vapor-grown to form a polycrystalline silicon rod having a desired diameter in an inverted U-shape.

As described above, the polycrystalline silicon produced by the Siemens method is used as a raw material of single crystal silicon for semiconductors or silicon for solar cells. These require a high purity polycrystalline silicon having a low impurity concentration. Therefore, raw material gases used in the Siemens method and members used in a furnace are required to have high purity.

Under such circumstances, various proposals have been made on quality evaluation methods.

EP 2636767 A1 discloses a small-sized reactor device for experiments in which a raw material gas is introduced online to grow polycrystalline silicon so that quality evaluation is performed.

JP 2016-145118 A discloses an apparatus and an evaluation method that can perform an evaluation by depositing single crystal silicon in order to evaluate members in a furnace used for the Siemens method.

In addition, as a production method of polycrystalline silicon, JP H03-252397 A proposes, as a rod-shaped polycrystalline silicon for producing single crystal silicon by a floating zone melting method, polycrystalline silicon characterized in that single crystal grains in an outer peripheral part of a coarsened region having coarsened single crystal silicon grains are refined in an area equal to or larger than a minimum cross section of a melting zone at the time of floating zone melting.

SUMMARY OF INVENTION

Problem to be Solved by Invention

In EP 2636767 A1, a small piece of polycrystalline silicon is produced to perform a quality evaluation However, as described in EP 2636767 A1, polycrystalline silicon as it is cannot be subjected to an evaluation of a low concentration of impurities that is performed by, for example, the photoluminescence method or Fourier transform infrared spectroscopy. Therefore, an additional operation such as single crystallization of the obtained polycrystalline silicon or the like is required. In addition, in that case, it is also necessary to consider segregation with respect to impurities when the single crystallization is performed.

In JP 2016-145118 A, single crystal silicon is grown and evaluated in order to evaluate inorganic materials used for members of a polycrystalline silicon manufacturing apparatus and to evaluate impurity concentrations of low concentration impurities. However, in the embodiment described in JP 2016-145118, a raw material gas flows in one pass similarly to the case of epitaxial growth, and the raw material gas cannot be in an environment like an actual polycrystalline silicon manufacturing environment in which a gas circulating in a furnace ascends together with the raw material gas. In addition, it is necessary to make new equipment to grow single crystal silicon for evaluation of inorganic materials, thereby leading to an increase in cost.

Although JP H03-252397 A proposes a manufacturing method of polycrystalline silicon having coarsened single crystal silicon grains, the purpose of the method is merely to improve a melting state at the time of floating zone melting, and the technique has not been used in a region of an evaluation method.

The present invention has been made in view of such a problem, and an object of the present invention is to provide a quality evaluation method, a manufacturing method of silicon for evaluation, silicon for evaluation, and a manufacturing system of silicon for evaluation that can easily perform quality evaluation.

Means for Solving Problem

[Concept 1]

A quality evaluation method may comprise:

- a step of producing a silicon for evaluation in which a single crystal silicon is grown to extend radially from a core wire while polycrystalline silicon is grown in a reactor; and
- a step of performing an evaluation using the single crystal silicon.

[Concept 2]

The quality evaluation method according to concept 1 may further comprise a step of taking out the silicon for evaluation from the reactor,

- wherein the evaluation may be performed using the single crystal silicon of the silicon for evaluation taken out from the reactor.

[Concept 3]

In the quality evaluation method according to concept 1 or 2, a plurality of pieces of silicon for evaluation may be produced under same conditions except a growth time, and the evaluation for each silicon for evaluation may be performed.

[Concept 4]

In the quality evaluation method according to any one of concepts 1 to 3, the core wire may be a single crystal silicon core wire, and a method for growing the polycrystalline silicon on the single crystal silicon core wire may be a Siemens method.

[Concept 5]

In the quality evaluation method according to any one of concepts 1 to 4, wherein an evaluation target in the silicon for the evaluation may be any one or more than one of P, As, B, Al, and C.

[Concept 6]

A manufacturing system of silicon for evaluation may comprise:

a supply pipe that supplies raw material gas;

a plurality of reactors for evaluation that are connected to the supply pipe, in each of which a silicon for evaluation is produced by growing a single crystal silicon to extend radially from a core wire while polycrystalline silicon is grown; and a control unit that controls a supply of the raw material gas to each reactor for evaluation, wherein a timing of starting and stopping a supply of the raw material gas to the reactors for evaluation may be differentiated by a command from the control unit.

[Concept 7]

The manufacturing system of silicon for evaluation according to concept 6 may further comprise a normal reactor in which polycrystalline silicon is grown, wherein growth of the polycrystalline silicon in the normal reactor and growth of the silicon for evaluation in the reactors for evaluation may be performed simultaneously.

[Concept 8]

A manufacturing method of a silicon for evaluation, when polycrystalline silicon may be grown on a silicon core wire, a single crystal silicon is grown in a growth direction from a surface of the silicon core wire, and the single crystal continues to grow to at least 5 mm from an outer periphery of the polycrystalline silicon.

[Concept 9]

In the manufacturing method of a silicon for evaluation according to concept 8, the single crystal may continue to grow to at least 3 mm from the outer periphery of the polycrystalline silicon.

[Concept 10]

A silicon for evaluation, wherein single crystal silicon may extend in a growth direction from a surface of a core wire, and wherein a part or all on an outer side of the single crystal silicon may be surrounded by a polycrystalline silicon in a cross-section.

[Concept 11]

In the silicon for evaluation according to concept 10, the single crystal may extend from the surface of the core wire to at least 5 mm from an outer periphery of the polycrystalline silicon.

[Concept 12]

In the silicon for evaluation according to concept 10, the single crystal may extend from the surface of the core wire to at least 3 mm from an outer periphery of the polycrystalline silicon.

[Concept 13]

In the silicon for evaluation according to any one of concepts 10 to 12, wherein a length of growth of the single crystal may be less than or equal to 30 mm.

When the present invention is applied to a quality evaluation of polycrystalline silicon, the evaluation can be easily performed while the cost is reduced.

DETAILED DESCRIPTION

Hereinafter, an embodiment for carrying out the present invention will be described.

Figure 1:
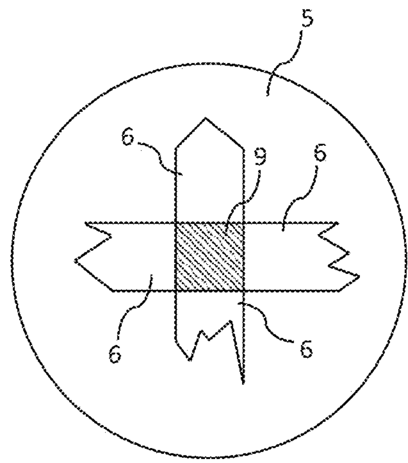
FIG. 1 is a transverse sectional view of polycrystalline silicon according to an embodiment of the present invention inside which single crystal silicon parts are formed.
Figure 2:
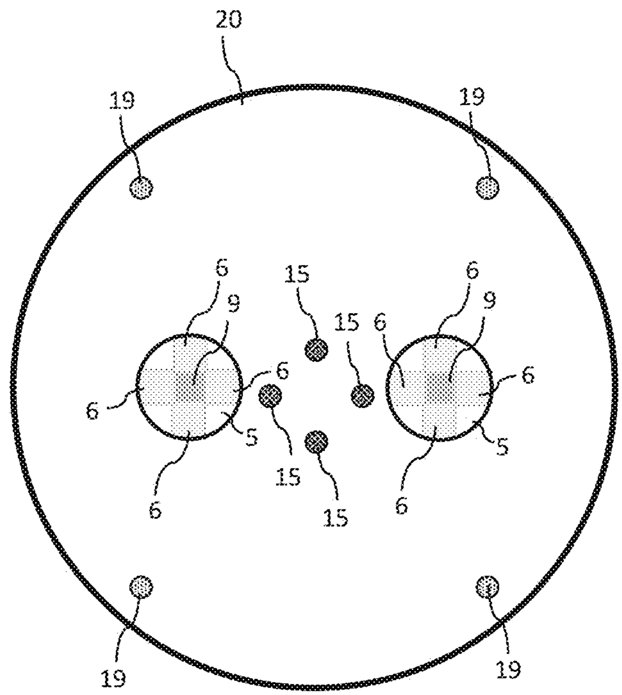
FIG. 2 is a transverse sectional view of a reactor in the embodiment of the present invention.

The quality evaluation method of the present embodiment may include a step of producing silicon for evaluation in which while polycrystalline silicon is grown on each core wire 9 in the reactors 20 and 40 (see FIG. 3), single crystal silicon radially extending from each core wire 9 (in the present embodiment, the single crystal silicon is referred to as "single crystal silicon parts 6") is produced (see FIGS. 1 and 2); and a step of performing an evaluation using the single crystal silicon parts 6. A method for growing polycrystalline silicon on the single crystal silicon core wire 9 may be the Siemens method. By adjusting a raw material gas and rising and falling conditions of temperature, the single crystal silicon parts 6 extending radially from each core wire 9 can be produced while polycrystalline silicon is grown. The bottom surface of each of the reactors 20 and 40 is provided with supply nozzles 15 through which the raw material gas is supplied from a supply pipe 10 (see FIG. 3) and is provided with discharge ports 19 through which the raw material gas and the like that have not been used to grow polycrystalline silicon is discharged (see FIG. 2). Although FIG. 2 illustrate a small-sized evaluation reactor 20, the normal-sized (large-sized) normal reactors 40 are each provided with a larger number of supply nozzles 15 and discharge ports 19 than as shown in FIG. 2.

In the present embodiment, the single crystal silicon parts 6 generated in the process of generating polycrystalline silicon are used. However, after a predetermined time has elapsed, the content ratio of polycrystalline silicon increases, and polycrystallization proceeds (the content ratio of a polycrystalline silicon part 5 increases), so that a polycrystalline silicon rod made of polycrystalline silicon is finally produced. As illustrated in FIG. 1, the polycrystalline silicon part 5 is formed at the peripheral edge of the single crystal silicon parts 6.

There may be a step of taking out the silicon for evaluation from the reactors 20 and 40. In this case, the evaluation may be performed using the single crystal silicon parts 6 of the silicon for evaluation taken out from the reactors 20 and 40. It is considered that the evaluation according to the present embodiment is mainly used for evaluation of a contained amount of impurities (evaluation of a raw material gas). Note that it generally takes several days to grow single crystal silicon from polycrystalline silicon. However, the present embodiment enables an operation using a small-sized floating zone melting (FZ) apparatus to be performed in a remarkably short time, and the present embodiment is therefore very advantageous in that it is possible to rapidly perform an evaluation using the single crystal silicon parts 6. Specifically, in the present embodiment, an evaluation can be performed using the single crystal silicon parts 6 formed under respective ones of growth conditions while polycrystalline silicon is grown; therefore, it is very advantageous in that the impurities and the like contained in the single crystal silicon parts 6 can be efficiently evaluated at low cost.

Figure 3:
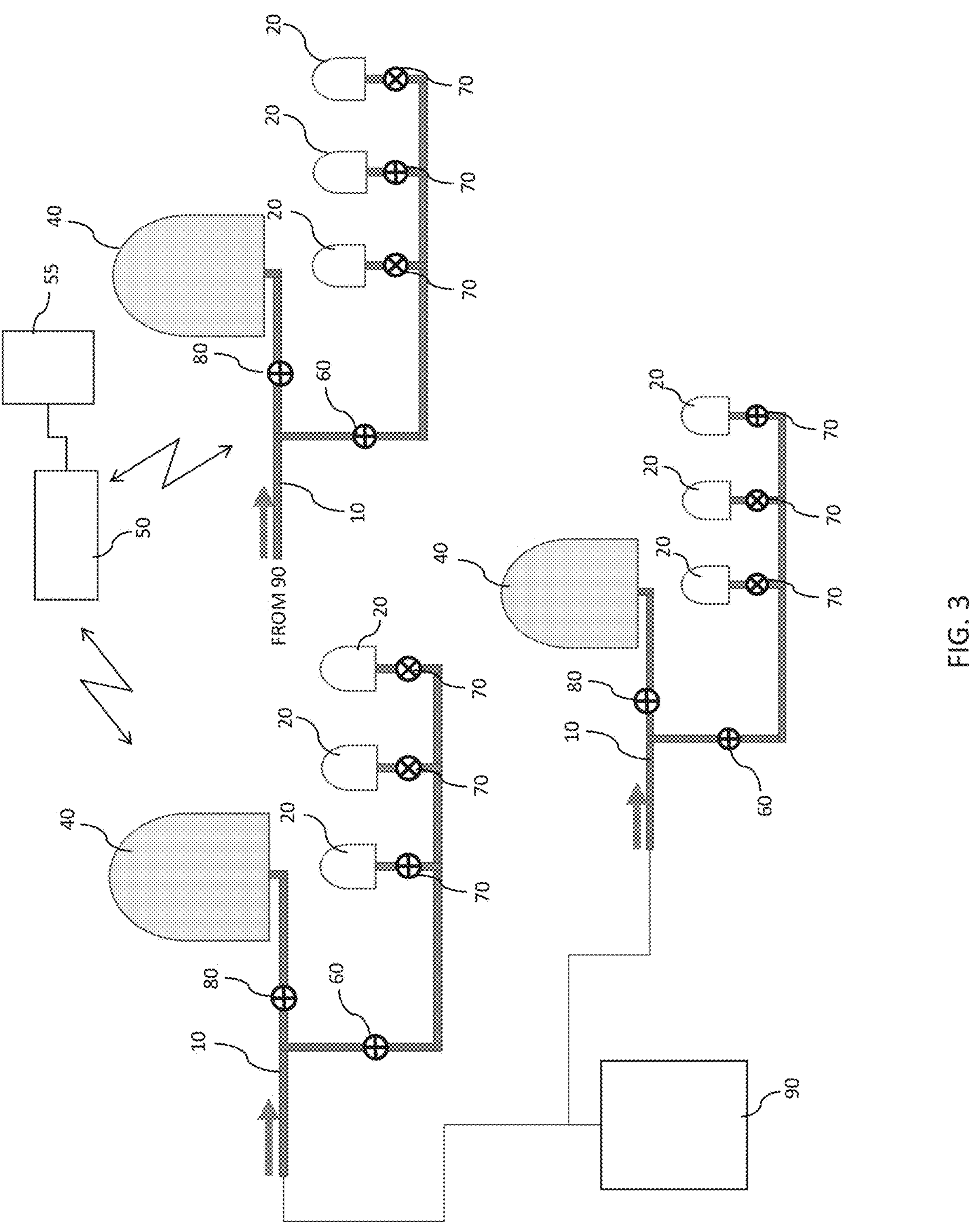
FIG. 3 is a schematic view illustrating an example of a manufacturing system of silicon for evaluation used in the embodiment of the present invention.

As shown in FIG. 3, a plurality of reactors 20 and 40 may be used. FIG. 3 illustrates an evaluation system including: a supply pipe 10 for supplying a raw material gas such as trichlorosilane (TCS); normal reactors 40 each connected to the supply pipe 10; and a plurality of evaluation reactors 20 (three reactors for one normal reactor 40 in FIG. 3) connected to the supply pipe 10. A sub opening and closing unit 70 is provided between the branched supply pipe 10 and each of the evaluation reactors 20, so that an inflow amount of the raw material gas supplied into each evaluation reactor 20 and opening and closing of each sub opening and closing unit 70 can be individually controlled. In addition, a first main opening and closing unit 60 is provided in the supply pipe 10 connected to each evaluation reactor 20 after being branched to the normal reactors 40 and the evaluation reactors 20, so that the inflow amount and opening and closing of the raw material gas supplied into the evaluation reactors 20 can be collectively controlled. In addition, a second main opening and closing unit 80 is provided on the supply pipe 10 connected to each normal reactor 40, and the inflow amount and opening and closing of the raw material gas supplied into the normal reactor 40 can be controlled. By closing a second main opening and closing units 80, only the evaluation using silicon for evaluation can be performed using only the evaluation reactors 20. A control unit 50 may be connected to the sub opening and closing units 70, the first main opening and closing units 60, and the second main opening and closing units 80 in a wired or wireless manner, and the above-described control of the sub opening and closing units 70, the first main opening and closing units 60, and the second main opening and closing units 80 may be performed in response to a command from the control unit 50.

With the aspect illustrated in FIG. 3, the growth of polycrystalline silicon in the normal reactors 40 and the growth of silicon for evaluation in the plurality of evaluation reactors 20 can be performed simultaneously.

The timing of stopping the supply of the raw material gas to each of the evaluation reactors 20 can be differentiated by a command from the control unit 50. In addition, not the timings of stopping the supply of the raw material gas, but the timings of starting the supply may be differentiated to produce different silicon for evaluation. In addition, by differentiating the timing of starting the supply of the raw material gas to each of the evaluation reactors 20 and by stopping the supply of the raw material gas, different silicon for evaluation may be produced. In any case, by supplying the raw material gas containing the same components to each of the evaluation reactors 20, it is possible to compare more reliably between pieces of silicon for evaluation.

The control unit 50 may be connected to the plurality of evaluation reactors 20 and the plurality of normal reactors 40 in a wireless or wired manner to control temperatures of the plurality of evaluation reactors 20 and the plurality of normal reactor 40. In one example, the control may be performed as follows. The temperature of each of the plurality of evaluation reactors 20 and the plurality of normal reactors 40 is varied in the same way, the raw material gas is commonly supplied to each of the plurality of evaluation reactors 20 and the plurality of normal reactors 40, and only the timings of stopping the supply of the raw material gas to the plurality of evaluation reactors 20 and the plurality of normal reactors 40 are differentiated. Therefore, it is possible to compare temporal changes of the silicon for evaluation produced in respective ones of the evaluation reactors 20, and it is possible to compare to analysis results (measurement results of concentration of impurities included in the radial direction or other measurement results) of polycrystalline silicon generated in the normal reactors 40.

The control unit 50 is connected to a storage 55, and may perform control on the basis of a recipe stored in the storage 55. The raw material gas is supplied from a raw material gas supply unit 90, and the following control may be performed on the basis of the recipe stored in the storage 55: control regarding the supply of the raw material gas from the raw material gas supply unit 90; and control regarding opening and closing of the sub opening and closing units 70, the first main opening and closing units 55, and the second main opening and closing units 80. The supply of the raw material gas to each of the plurality of evaluation reactors 20 may be stopped by the control unit 50 issuing a command to close the corresponding sub opening and closing unit 70 on the basis of the recipe stored in the storage 55.

In the present embodiment, polycrystalline silicon of a normal size (large size) is produced in the normal reactors 40, and small-sized silicon for evaluation (whose diameter may be about 30 mm to 60 mm) is produced in each of the plurality of evaluation reactors 20. At this time, polycrystalline silicon and a plurality of pieces of silicon for evaluation are produced under the same conditions except the growth time.

Conventionally, the produced polycrystalline silicon is analyzed in the radial direction, and the timing at which impurities have entered the polycrystalline silicon is estimated from the position of the included impurities in the radial direction. However, in the case of adopting the present aspect, the growth of polycrystalline silicon in silicon for evaluation can be stopped at an appropriate timing by, for example, closing the sub opening and closing unit 70, and the impurities included in the silicon for evaluation can be evaluated as appropriately. Therefore, a specific evaluation can be performed with respect to the timing at which impurities are included.

In recent years, a demand with respect to impurity concentrations has become strict, and impurity concentrations as follows are problematic: an impurity concentration on the order of several to several tens of ppta with respect to B and P; and an impurity concentration on the order of several to several tens of pptw with respect to heavy metal concentrations. Therefore, it is an extremely useful analysis means to check, in real time as in the present embodiment, the timing at which impurities are included, and the present embodiment makes it possible to extremely effectively determine growth conditions of single crystal silicon, which determination is difficult with the conventional method. For example, in the case where a system as shown in FIG. 3 is adopted, it is possible to prevent or reduce wasteful consumption of material and time by performing temporal observation in the evaluation reactors 20 and by stopping the reaction in the other evaluation reactors 20 and the normal reactors 40 when the amount of impurities increases.

As the evaluation reactors 20 used for manufacturing silicon for evaluation in the present embodiment, small reaction furnaces for experiments may be used. Specifically, the manufacturing of silicon for evaluation can be performed in an aspect like a small-sized reaction furnace shown in EP 2636767 A1. The bell jars are preferably made of quartz or the like in consideration of prevention of contamination.

Referring to the method described in JP H03-252397 A as a manufacturing method of silicon for evaluation, polycrystalline silicon containing the single crystal silicon parts 6 may be grown up to a required diameter.

In the present embodiment, the single crystal silicon parts 6 can be partially produced in the process of producing polycrystalline silicon. Therefore, the single crystal silicon parts 6 can be used in case of performing an evaluation for which single crystal silicon is required. In addition, it is very advantageous in that an evaluation can be performed using the single crystal silicon parts 6 formed in polycrystalline silicon as it is without taking the trouble of producing single crystal silicon.

As illustrated in FIG. 1, when viewed in a cross-section cut in the direction orthogonal to the direction in which the polycrystalline silicon extends, the single crystal silicon parts 6 may be provided to extend in the growth direction in the radial direction from the surface of each core wire 9, and part or all on the outer side of the peripheral edge of the single crystal silicon parts 6 may be surrounded by the polycrystalline silicon part 5.

When the polycrystalline silicon is grown on the core wire 9, the single crystal silicon parts 6 may be grown in the growth direction from the surface of the silicon core wire 9, and the single crystal may be allowed to continue to grow to at least 5 mm from the outer periphery of the polycrystalline silicon part 5 formed to surround the single crystal silicon parts 6. The single crystal may be allowed to continue to grow to at least 3 mm from the outer periphery of the polycrystalline silicon part 5. As a result, it is possible to obtain silicon for evaluation in which the single crystal silicon parts 6 extend to at least 5 mm or at least 3 mm from the outer periphery of the polycrystalline silicon part 5

The single crystal silicon parts 6 may grow to have a diameter less than or equal to 30 mm. In this case, the single crystal silicon parts 6 extending in the radial direction of the polycrystalline silicon from the surface of the silicon core wire 9 extend less than or equal to 30 mm. A raw material evaluation is required for both CZ and FZ, and it is advantageous to use an aspect in a small size as in the present aspect because an evaluation cost can be reduced.

In the grown polycrystalline silicon, when the crystal face directed to a certain orientation is chosen as the side surface of the core wire 9, single crystal silicon parts 6 grows in the growth directions. The core wire 9 to be used is preferably cut out such that the <110> plane is a side surface of the core wire 9, and is used. The polycrystalline silicon part 5 grows in the periphery of the single crystal silicon parts 6 and in diagonal directions of the cross-section of the core wire 2. In the case where the single crystal silicon parts 6 are required, the single crystal silicon parts 6 can be used, and otherwise, the polycrystalline silicon part 5 can be used.

When the resistivity of the single crystal silicon parts 6 is measured, the four-probe method may be used. Because the resistivity cannot be measured in the polycrystalline silicon part 5, it is advantageous to partially produce the single crystal silicon parts 6 as in the present embodiment.

The evaluation target in the silicon for evaluation may be any one or more than one of P, As, B, Al, and C. When a donor or an acceptor such as P, As, B, or Al is evaluated, a photoluminescence method is generally used. As the photoluminescence method, the method disclosed in JP 2016-145118 A may be used. Also in the photoluminescence method, it is necessary to measure single crystal silicon, and the present embodiment is advantageous in that evaluation can be performed using the single crystal silicon parts 6.

When C is evaluated, Fourier transform infrared spectroscopy is generally used to measure Cs representing substituted carbon. Also in this case, it is necessary to measure single crystal silicon, and the present embodiment is advantageous in that an evaluation can be performed using the single crystal silicon parts 6.

When heavy metals are evaluated, the inductively coupled plasma mass spectrometry is generally used. In this case, a sample is dissolved in a fluoronitric acid and an analysis is performed, and therefore, the analysis does not depend on whether the sample is single crystal or polycrystalline. Therefore, the evaluation can be performed using a polycrystalline silicon region (polycrystalline silicon part 5) of the silicon for evaluation. It is preferable, but not limited thereto, to evaluate the polycrystalline silicon part 5 similar to polycrystalline silicon that is actually being manufactured, and the single crystal silicon parts 6 may be used to perform the evaluation.

In addition, with the present embodiment, the silicon for evaluation has both the single crystal silicon parts 6 and the polycrystalline silicon part 5, and therefore the single crystal silicon parts 6 or the polycrystalline silicon part 5 can be selected depending on the necessity in the evaluation.

The present embodiment can also be employed in a case where the raw material gas is evaluated online with respect to the actual normal reactor 40 (see FIG. 3). In addition, the present embodiment can be adopted when evaluation requiring single crystal silicon is performed in a case where members are evaluated or in other cases.

When members are evaluated, it can be checked how an actual normal reactor 40 is affected, by performing calculation, in terms of surface area or volume for each member, with respect to use amounts in the actual normal reactor 40.

Example

Trichlorosilane as the raw material was collected from the same tank into a cylinder as the raw material gas supply unit 90. Part of trichlorosilane from the raw material gas supply unit 90 was supplied to the normal reactor 40 in which epitaxial growth can be performed to produce single crystal silicon. The remaining part of the trichlorosilane from the raw material gas supply unit 90 was supplied to the small evaluation reactor 20. A hydrogen gas was similarly introduced to each reactor to grow crystal.

As a result of evaluating the single crystal silicon parts 6 obtained when epitaxial growth of polycrystalline silicon is performed in the normal reactor 40 and the single crystal silicon parts 6 obtained when polycrystalline silicon is grown in the evaluation reactor 20, it has been found that the both single crystal silicon parts 6 can be evaluated identically.

With the present invention, it is possible to deal with an evaluation method in which single crystal silicon is required, without additional cost.

REFERENCE SIGNS LIST

5 polycrystalline silicon part
6 single crystal silicon part
9 core wire
20 evaluation reactor
40 normal reactor

The invention claimed is:

1. A silicon for evaluation, wherein single crystal silicon extends in a growth direction from a surface of a single crystal silicon core wire, and wherein a part or all on an outer side of the single crystal silicon is surrounded by a polycrystalline silicon in a cross-section.

2. The silicon for evaluation according to claim 1, wherein the single crystal extends from the surface of the single crystal silicon core wire to at least 5 mm from an outer periphery of the polycrystalline silicon.

3. The silicon for evaluation according to claim 1, wherein the single crystal extends from the surface of the single crystal silicon core wire to at least 3 mm from an outer periphery of the polycrystalline silicon.

4. The silicon for evaluation according to claim 1, wherein a length of growth of the single crystal is less than or equal to 30 mm.

* * * * *